United States Patent

Huber et al.

[11] 4,041,230
[45] Aug. 9, 1977

[54] FLAMEPROOFED MODACRYLIC COPOLYMERS OF UNSATURATED CARBOXY-PHOSPHINIC ACID DERIVATIVES

[75] Inventors: Bernd Huber, Hofheim, Taunus; Hans-Jerg Kleiner, Kronberg, Taunus, both of Germany

[73] Assignee: Hoechst Aktiengesellschaft, Frankfurt am Main, Germany

[21] Appl. No.: 623,335

[22] Filed: Oct. 17, 1975

[30] Foreign Application Priority Data

Oct. 19, 1974 Germany .............................. 2449469
Oct. 19, 1974 Germany .............................. 2449466

[51] Int. Cl.$^2$ ..................... C08F 30/02; C08F 230/02;
                                   C08F 26/06; C08F 4/30
[52] U.S. Cl. .................................. 526/278; 260/32.4;
                            260/79.3 MU; 260/956; 526/225; 526/229;
                                                                526/258
[58] Field of Search ...................... 526/278, 258, 229;
                                                        260/79.3 MU

[56] References Cited
U.S. PATENT DOCUMENTS

| | | | |
|---|---|---|---|
| 3,197,497 | 7/1965 | Mark | 526/278 |
| 3,282,904 | 11/1966 | Marktscheffel | 526/278 |
| 3,312,674 | 4/1967 | Welch | 526/278 |
| 3,766,252 | 10/1973 | Schmidt | 526/278 |

*Primary Examiner*—Herbert J. Lilling
*Attorney, Agent, or Firm*—Curtis, Morris & Safford

[57] ABSTRACT

Carboxylic acid derivatives of the formula (I)

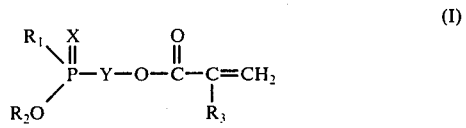

where $R_1$ and $R_2$ are alkyl or haloalkyl radicals having a total of up to 8 carbon atoms, $R_3$ is hydrogen or methyl, X is oxygen or sulfur and Y is linear or branched alkylene having up to 6 carbon atoms, a process for their manufacture and filaments and fibers on the basis of modacrylic polymers wherein the fiber-forming substance comprises a copolymer of 35 to 85% by weight of acrylonitrile
5 to 45% by weight of vinyl chloride, vinyl bromide, vinylidene chloride or a mixture thereof, and
5 to 30% by weight of a carboxyphosphinic acid derivative of the formula I and 0 to 15% by weight of other unsaturated compounds with activated double bond, and a process for their manufacture. The filaments and fibers are self-extinguishing, have a good thermostability and a high degree of whiteness.

5 Claims, No Drawings

FLAMEPROOFED MODACRYLIC COPOLYMERS OF UNSATURATED CARBOXY-PHOSPHINIC ACID DERIVATIVES

The present invention relates to novel unsaturated phosphorus containing carboxylic acid derivatives of the formula (I)

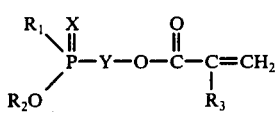

in which $R_1$ and $R_2$ represent lower alkyl or haloalkyl radicals having a total of up to 8 carbon atoms, $R_3$ is a hydrogen atom or a methyl group, X stands for an oxygen or a sulfur atom and Y represents a branched or linear alkylene group having from 1 to 6 carbon atoms, and to flame-resistant fibers and filaments of copolymers of acrylonitrile with vinyl chloride, vinyl bromide and/or vinylidene chloride, which copolymers are modified with carboxyphosphinic acid derivatives of the formula I.

Unsaturated phosphorus containing carboxylic acid derivatives of the formula

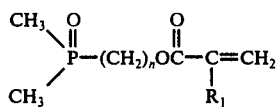

where $R_1$ is hydrogen or methyl and $n$ is 1, 2 or 3, are already known (German Offenlegungsschrift No. 2,052,569). They are derivatives of tertiary phosphine oxides which have good flame retarding properties. Starting product for their preparation is generally dimethylchlorophosphine which, simultaneously with methyldichlorophosphine, is obtained in the industrial-scale process of reacting methyl chloride with phosphorus at about 350° C (German Auslegeschrift No. 1 568 928). A similar flameproofing application as described above for dimethylchlorophosphine is unknown hitherto for methyldichlorophosphine, which makes the above use of dimethylchlorophosphine uneconomic.

The present invention now provides novel phosphorus containing carboxylic acid derivatives of the formula (I)

The present invention provides furthermore a process for the preparation of compounds of formula (I), which comprises reacting alcohols of the formula (II)

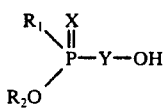

wherein $R_1$, $R_2$, X and Y are as defined above, with compounds of the formula (III)

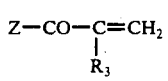

where Z is halogen, perferably chlorine; and $R_3$ is as defined above, in the presence of an inert solvent.

The acylation according to the invention of alcohols of formula (II) with acrylic or methacrylic acid halides of formula (III) is carried out in known manner, preferably in the presence of a hydrogen halide-binding compound, for example a tertiary amine such as triethylamine or pyridine, at temperatures of from −30° to +100° C, preferably from 20° to 70° C. The hydrogen halide-binding compound is used in equimolar amounts relative to the acid halide of formula (III), or in a slight excess of up to about 10%.

It is furthermore preferable to use one of the polymerization inhibitors known for acrylic acid derivatives, for example phenothiazine, hydroquinone, hydroquinone-monomethyl ether and/or metal salt inhibitors. The amount of inhibitor is chosen within the usual range, for example from 0.01 to 1 weight %, relative to the compound of formula (III). The presence of active polymerization inhibitors is important also for the optional distillation work-up of the crude reaction mixture.

The starting compounds of formula (II) and (III) are generally used in about equimolar amounts; the acid halide of formula (III) optionally being in a slight excess of up to 10%. The conversion of the reactants is carried out with exclusion of water.

The reaction is advantageously carried out as follows: the alcohol of formula (II) and the tertiary amine optionally used in the inert solvent are introduced first into the reactor at room temperature, and the acid chloride of formula (III) is added dropwise, while the batch is continuously and thoroughly intermixed, for example by means of an agitator.

The reaction temperature is not critical and may rise within the abovementioned temperature range, that is, up to 100° C because of the reaction heat set free during the reaction, and this may be advantageous for the course of the reaction. The starting compounds of formula (II) are easily obtainable. For example, hydroxymethyl-alkylphosphinic acid esters are prepared by addition of paraformaldehyde on alkylphosphonous acid esters according to the process of German Offenlegungsschrift No. 2 226 406. 2-Hydroxyethyl-alkylphosphinic acid esters are obtained with good yields from 2-acetoxy ethyl-alkylphosphinic acid esters according to the process of German Offenlegungsschrift No. 2 335 852, and 3-hydroxypropylalkylphosphinic acid esters may be prepared in analogous manner.

Typical phosphorus containing carboxylic acid derivatives of formula (I) are for example: the acrylic and methacrylic acid esters of methylhydroxymethylphosphinic acid methyl, ethyl, propyl or isobutyl ester; ethyl-hydroxymethylphosphinic acid methyl, ethyl, propyl, or isobutyl ester; methyl-2-hydroxyethylphosphinic acid isobutyl ester; methyl-2-hydroxyethylthiophosphinic acid isobutyl ester; propyl-2-hydroxyethylphosphinic acid propyl ester; methyl-(2-hydroxy-2-methylethyl)-phosphinic acid methyl, ethyl, propyl, n-butyl, isobutyl or pentyl ester; methyl-3-hyroxypropylphosphinic acid isobutyl ester; butyl-3-hydroxypropylphosphinic acid isopropyl ester.

An inert solvents there may be used for example those solvents which are usually employed for esterification and/or ester interchange, such as benzene, toluene, xylene, chlorobenzene, carbon tetrachloride, chloroform, diisopropyl ether, acetonitrile or mixtures of such compounds. The amount of inert solvent is not critical and depends advantageously on the agitatability of the reaction batch after complete reaction, in which the hydrogen halide-binding compound optionally used precipitates generally as a hydrohalide in the form of crystals. Therefore, the inert solvent is generally used in a weight amount of up to 10 times, preferably from 2 to 5 times, that of the alcohol of formula (II). Xylene or toluene are the preferred inert solvents.

Because of their unsaturated carbon-carbon bonds, the novel carboxylic acid derivatives of formula (I) are suitable as monomers or comonomers for the preparation of polymers. For example, by copolymerization with monomers such as acrylic derivatives, styrene or vinyl compounds, flame retarding polymers having improved dyeability and antistatic properties are obtained. As shown below copolymers consisting of acrylonitrile, vinyl chloride, vinyl bromide and/or vinylidene chloride and compounds of formula (I) have surprisingly good flame retarding properties. Furthermore, filaments and fibers made from these copolymers have an unexpected high thermostability, that is, their tendecy to yellowing under thermal strain is considerably reduced as compared to the state of the art.

By ester interchange of the phosphinic acid ester groups $OR_2$ (preferably in the case of $R_2$ being alkyl having from 1 to 4 carbon atoms, especially methyl or ethyl) with glycols such as ethylene glycol, diethylene glycol, propylene glycol or higher glycols, the polymers obtained may also be cross-linked. When using methyldichlorophosphine as starting material, the phosphinic acid esters of formula (I) are more easily obtainable than the analogous tertiary phosphine oxides, which require the use of dimethylchlorophosphine as starting substance. Contrary to dimethylchlorophosphine, methyldichlorophosphine is easily manufactured on an industrial scale, since it may be obtained in known manner and as exclusive product by reaction of methane with $PCl_3$ at 600° C.

It is general knowledge to render polymers flame-resistant by the addition or incorporation of phosphorus-containing compounds. So far vinyl or allyl phosphonic acid derivatives have been proposed as phosphorus-containing modifying agents. In German Offenlegungsschrift 2,052,568 carboxylic acid derivatives of phosphine oxide are described. U.S.S.R. Pat. No. 168,438 discloses the use of carboxyphosphonic acid and carboxyphosphinic acid derivatives for the manufacture of flame-resistant polystyrene.

It has been observed that the flame resistance of copolymers of acrylonitrile with vinyl bromide, vinylidene chloride and/or vinyl chloride can be considerably improved by adding derivatives of phosphine oxide, while the corresponding phosphonic acid derivatives practically do not improve the flame resistance by synergism. A drawback of the polymers and especially of the filaments and fibers produced therewith, which have been modified with the phosphine oxide derivatives according to the process described in German Offenlegungsschrift No. 2,052,568, is, however, their poor thermostability.

It has now surprisingly been found that copolymers of acrylonitrile with vinyl chloride, vinyl bromide and/or vinylidene chloride which have been modified with carboxy-phosphinic acid derivatives and the filaments and fibers of these polymers have a considerably improved thermostability with a comparable flame-resistance. Consequently, the filaments and fibers made from the said polymers have a much lower tendency to turn yellow at elevated temperature than the hitherto known modacrylic filaments and fibers modified with flame retardants. The term modacrylic fibers is intended to include multi-polymer fiber material composed of at least 35% by weight and at most 85% by weight of acrylonitrile units.

The filaments and fibers which have been modified according to the invention are obtained spinning products obtained by copolymerizing acrylonitrile and optionally other unsaturated compounds having an activated double bond with vinyl chloride, vinyl bromide and/or vinylidene chloride and carboxy-phosphinic acid derivatives according to the above formula I. The copolymers from which the filaments and fibers are made preferably contain from 5 to 45% by weight of vinyl chloride, vinyl bromide and/or vinylidene chloride units and 5 to 30% by weight of units derived from compounds of formula I, the percentages by weight being calculated on the total polymer.

Filaments and fibers having optimum properties are obtained from a fiber material prepared by copolymerization of acrylonitrile and optionally further unsaturated compounds with activated double bond with 10 to 30% by weight of vinyl chloride, vinyl bromide and/or vinylidene chloride and 8 to 20% by weight of carboxy-phosphinic acid derivatives of formula I.

The copolymers used for making the filaments and fibers according to the invention can be prepared, for example, with the use of the phosphorus-containing carboxylic acid derivatives of formula I, mentioned above on page 5.

The polymerization of the phosphorus-containing carboxylic acid derivatives of formula I with acrylonitrile and other unsaturated compounds with activated double bond is carried out according to any copolymerization process known for acrylonitrile, i.e. with the action of ionic, free radical or redox catalysts, either in solution or in dipersion, by solution, bead or precipitation polymerization or by mass polymerization. In general, free radical or redox polymerization is preferred to ionic polymerization which gives lower degrees of polymerization and lower yields especially in the case of acrylic acid esters.

Suitable catalyst systems are, for example, hydrogen peroxide, potassium or ammonium peroxo potassium or ammonium peroxo disulfate, dibenzoyl peroxide, tert. butyl hydroperoxide, di-tert. butyl peroxide, and other organic peroxides; diazomethane, azoisobutyric acid dinitrile and derivatives thereof, diazonium and diazo compounds, inorganic and organic peroxides in combination with ferrous salts, sodium bisulfite, sulfinic acids, or mercaptans. The polymerization can also be initiated by radical forming radiation.

As solvents or dilutents a great number of organic compounds can be used, for example dimethyl formamide, chlorobenzene, methanol, ethanol, i-propanol, or acetone. The polymerization is preferably carried out in an aqueous medium. When the polymerization is carried out in heterogeneous phase the usual emulsifiers and protective colloids can be added.

Suitable comonomers with activated double bond are, for example the following compounds: acryl amide, acrylic acid, and the esters thereof, vinyl esters and ethers, such as, for example, vinyl acetate, vinyl stearate, vinyl butyl ether, haloacetic acid vinyl esters such as bromoacetic acid vinyl ester, dichloroacetic acid vinyl ester, trichloroacetic acid vinyl ester, styrene, and maleic imide.

Experiments have shown that filaments and fibers made from polymers obtained by polymerization of carboxylic acid derivatives of the formula I with acrylonitrile alone exhibit a poor flame resistance. The flame resistance is optimized when halogen containing comonomers such as vinyl chloride, vinyl bromide and/or vinylidene chloride are incorporated besides acrylonitrile into the polymer. Only under these conditions are flame-resistant filaments or fibers obtained.

The polymers obtained are soluble in the solvents known for polyacrylonitrile, for example dimethyl formamide, dimethyl acetamide, dimethyl sulfoxide, or ethylene carbonate. The solutions prepared with the aforesaid solvents can be spun by the known wet spinning processes for polyacrylonitrile, for example by pressing the polymer solutions through a spinneret into a coagulation bath consisting of the solvent and a non solvent, drawing the filaments formed in further baths, freeing them from the solvent used and drying the filaments obtained. Owing to the good thermostability of the polymers of the invention they can also be spun into filaments and fibers by a known dry spinning process. Staple fibers are then obtained by cutting the two according to a known process.

The following examples illustrate the invention, the parts being by weight unless otherwise stated.

EXAMPLE 1

252 g (1.52 mol) of methylhydroxymethylphosphinic acid isobutyl ester, 153 g (1.52 mol) of triethylamine and 1 g of phenothiazine are dissolved in toluene and, with agitation and slight cooling, 137.5 g (1.52 mol) of acrylic acid chloride are added dropwise at 20° – 30° C. Agitation is continued for 15 hours. After one further hour, the triethylamine hydrochloride precipitated is suction-filtered. After having distilled off the solvent and after addition of polymerization inhibitors, the filtrate is distilled in vacuo. 185 g of

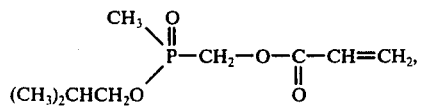

boiling point 95° – 98° C at 0.1 mm Hg, are obtained, which corresponds to a yield of 55.5% of the theoretical yield.

Analysis: found: C 49.3%; H 7.7%; P 14.0% calculated: C 49.1%; H 7.72%; P 14.1%.

EXAMPLE 2

500 g (2.78 mol) of methyl-2-hydroxyethylphosphinic acid isobutyl ester 281 g (2.78 mol) of triethylamine and 1.5 g of phenothiazine are dissolved in 1.67 l of toluene and, with vigorous agitation and without cooling, 252 g (2.78 mol) of acrylic acid chloride are added dropwise. The temperature rises to 50° C. After the chloride is added, agitation is continued for 15 hours. Subsequently, the batch is cooled to 10° C, and the triethylamine hydrochloride precipitated is eliminated by suction-filtration. After having distilled off the solvent in a water jet vacuum and after addition of polymerization inhibitors, the residue is distilled in vacuo. 485 g of

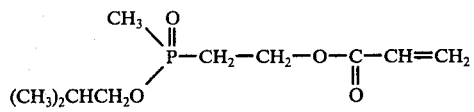

boiling point 145° C at 2mm Hg, are obtained, which corresponds to a yield of 75% of the theoretical yield.

Analysis: found: C 51.4; H 8.10% P 13.0% calculated: C 51.3%; H 8.12%; P 13.25%.

EXAMPLE 3

188 g (1.04 mol) of methyl-2-hydroxyethylphosphinic acid isobutyl ester, 105 g (1.04 mol) of triethylamine and 0.5 g of phenothiazine are dissolved in 620 ml of toluene and, with vigorous agitation and without cooling, 109 g (1.04 mol) of methacrylic acid chloride are added dropwise. The temperature rises to 50° – 60° C. After the chloride is added, agitation is continued for 10 hours, and the batch is cooled to −10° C. The triethylamine hydrochloride precipitated in the form of crystals is eliminated by suction-filtration, and the filtrate is substantially liberated from the toluene at 120° C and 35 mm Hg. After addition of polymerization inhibitors, the residue is distilled in vacuo. 220 g of

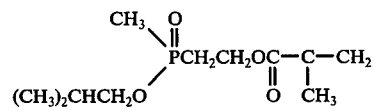

boiling point 125° – 131° C at 0.45 mm Hg, are obtained, which corresponds to a yield of 85%.

Analysis: found: C 53.2%; H 8.47%; P 12.5% calculated: C 53.6%; H 8.5%; P 12.4%

EXAMPLE 4

75 g (0.385 mol) of methyl-(2-hydroxy-2-methylethyl)-phosphinic acid isobutyl ester, 39 g of triethylamine (0.385 mol) and 0.3 g of phenothiazine are dissolved in toluene and, with slight cooling, 35 g (0.385 mol) of acrylic acid chloride are added dropwise. Agitation is continued for 12 hours. After a further hour, methylene chloride is added, and the triethylamine hydrochloride is suction-filtered. The filtrate, after having eliminated the solvent and added polymerization inhibitors, is distilled under reduced pressure. 57.5 g of

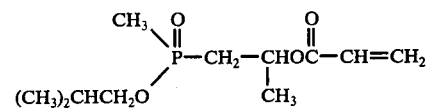

boiling point 95° – 100° C at 0.1 mm Hg, are obtained, which corresponds to a yield of 60% of the theoretical yield.

Analysis: found: C 53.4%; H 8.5%; P 12.5%; calculated: C 53.6%; H 8.5%; P 12.4%.

EXAMPLE 5

196 g (1 mol) of methyl-2-hydroxyethylthiophosphinic acid isobutyl ester, 101 g of triethylamine (1 mol) and 0.4 g of phenotiazine are dissolved in 500 ml of toluene and, with vigorous agitation and without cooling, 104.5 g (1 mol) of methacrylic acid chloride are added dropwise. The temperature rises to 50° C. Agitation is continued for 5 hours, and the batch is abandoned overnight. Subsequently, it is cooled, and the triethylamine hydrochloride is suction-filtered. The filtrate is stirred with water, the organic phase is separated and dried with Na₂SO₄. After having distilled off the solvent at room temperature and 1mm Hg, the residue, after addition of polymerization inhibitors, is distilled in a thin-layer evaporator at 180° C and 0.5 mm Hg. 200 g of

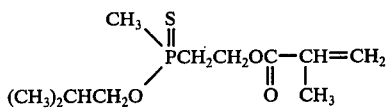

are obtained which corresponds to a yield of 76% of the theoretical yield.

Analysis: found: C 50.0%; H 7.90%; P 11.3%; S 12.05% calculated: C 50.0%; H 7.95%; P 11.75%; S 12.13%.

EXAMPLE 6

100 g (0.66 mol) of methyl-2-hydroxyethylphosphinic acid ethyl ester, 66.8 g (0.66 mol) of thiethylamine and 0.3 g of phenothiazine are dissolved in a mixture of toluene and methylene chloride, and, with vigorous agitation and cooling, 69 g (0.66 mol) of methacrylic acid chloride are added dropwise. After this addition is complete, agitation is continued for 1 hour, the batch is then cooled to 0° C, and is distilled in vacuo. 116 g of

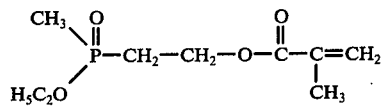

boiling point 147° C at 1.2 mm Hg, are obtained, which corresponds to a yield of 80% of the theoretical yield.

Analysis: found: C 49.2%; H 7.8%; P 14.1%; calculated: C 49.1%; H 7.8%; P 13.9%;

EXAMPLE 7

A one liter steel vessel was continuously charged with 250 ml/hr of a monomer mixture consisting of 71 parts acrylonitrile, 15 parts vinylidene chloride and 14 parts of a compound of the formula

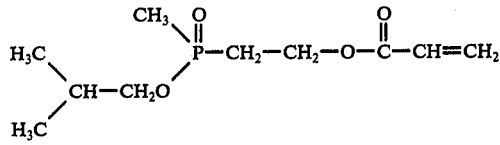

250 ml/hr of a solution of 10 g sodium acetate, 15 g sodium methallyl sulfonate and Mohr salt in 1.750 ml water, adjusted to pH 2.5 with sulfuric acid, and variable amounts of a solution of potassium peroxodisulfate in water and of a solution of sodium disulfite in water.

The proportion by weight of potassium peroxodisulfate to sodium disulfite was 1:4. The required amounts were determined by the desired degree of polymerization.

The polymerization was carried out at 55° C under pressure. The polymer suspension formed was continuously discharged after a residence time of 1 hour, the conversion obtained amounting to approximately 80%. The polymer was carefully washed and dried.

The relative viscosity was measured at 25° C in a 0.5% polymer solution in dimethyl formamide.

While stirring at 0° to −20° C the polymer was introduced into dimethyl formamide and stirring of the mixture was continued for 30 minutes at 60° C. The solution was then filtered and degassed. The spinning solution obtained had a polymer content of 15 to 30% by weight, calculated on the total solution. The solution was spun through a spinneret having 100 orifices each with a diameter of 80 microns into a coagulating bath consisting of 65% dimethyl formamide and 35% water and having a temperature of 30° C. The filaments obtained were drawn to about 4 times the original length in two further hot baths of diminishing dimethyl formamide content, washed with water and dried on hot godets. After drying, the filaments were drawn again by 25% of their length. The filaments obtained were drawn again by 25% of their length. The filaments obtained were then steamed at 110° C and a knitted hose was made therefrom on a circular knitting machine of Messrs. Velha.

The textile properties of the filaments indicated in the following Table 2 were measured after steaming. The knitted hose obtained was repeatedly washed, dried and its burning behavior was tested on a semi-circle tester according to DIN 54 331.

The thermostability was measured with the pulverulent polymer and the filaments spun therefrom.

The pulverulent polymer was passed through a sieve and then heated for 2 hours to 150° C in a drying cabinet. The fibers were likewise heated to a temperature of 150° C for 2 hours in a drying cabinet. After heating the brightness was measured in a reflectance photometer Elrepho of Messrs. Zeiss with a colorimetric filter FMY/C equalized against a calibrated MgO working standard.

The results obtained are indicated in the following Tables 1 and 2.

EXAMPLES 8 and 9

In the manner described in Example 7 further copolymers were prepared and filaments were spun therefrom. The variables and the results obtained are listed in the following Tables 1 and 2.

TABLE I

| Example No. | carboxyphosphinic acid derivative (PD) | monomer composition % by weight | viscosity η rel. | analytical values % P | analytical values % Cl | brightness % before heating | brightness % after 2 hrs. at 150° C |
|---|---|---|---|---|---|---|---|
| 7 | CH₃\P(=O)(O-i-but)—CH₂—CH₂—O—C(=O)—CH=CH₂ | 71% ACN 15% VCl₂ 14% PD | 2.4 | 1.6 | | 13.5 | |

TABLE I-continued

| Example No. | carboxyphosphinic acid derivative (PD) | monomer composition % by weight | viscosity η rel. | analytical values %P | analytical values %Cl | brightness % before heating | brightness % after 2 hrs. at 150° C |
|---|---|---|---|---|---|---|---|
| 8 | CH₃\P(=O)(i-but-O)—CH₂—CH₂—O—C(=O)—C(CH₃)=CH₂ | 70% ACN 15% VCl₂ 15% PD | 2.0 | 1.9 | 12.9 | 83.5 | 61.7 |
| 9 (comparison) | (CH₃)₂\P(=O)—CH₂—O—C(=O)—C(CH₃)=CH₂ | 75% ACN 15% VCl₂ 10% PD | a) 2.2 b) 1.9 | 1.7 1.8 | 13.0 13.4 | 85.3 85.1 | 23.0 21.9 |

ACN = acrylonitrile
VCl₂ = vinylidenechloride
PD = phosphorus derivative

TABLE 2

| | filaments | | | | | | knitted hose | | |
|---|---|---|---|---|---|---|---|---|---|
| Example | concentration of spinning sol. wt. % | titer tex | tensile strength g/tex | elongation at break % | residual DMF % | brightness % before heating | brightness % after 2 hrs. at 150° C | weight g/m² | stitches per cm² | burning test according to DIN 54 331 semi-circle tester |
| 7 | 20 | 44 | 18 | 35 | 0.26 | 73 | 38 | 570 | 150 | 6 out of 7 samples extinguished immediately after removal of the flame, burned distance 32° |
| 8 | 22 | 37 | 19 | 26 | 0.18 | 80 | 43 | 420 | 125 | all 7 samples extinguished immediately after removal of the flame, burned distance 30° |
| 9 | 24 | 41 | 21 | 31 | 0.20 | 76 | 23 | 440 | 120 | all 7 samples extinguished immediately after removal of the flame, burned distance 30° |

The results of the tables show that the thermostability of modacrylic filaments and fibers and of the copolymers from which they are made substantially depends on the type of the phosphorus derivative used. With an approximately equal phosphorus content in the copolymer the flame-resistance obtained is practically equal with the use of phosphinic acid derivatives and phosphine oxide derivatives but, after heating for a prolonged period of time, the copolymer modified with a phosphine oxide derivative is strongly colored as distinctly results from the values of brightness.

What is claimed is:

1. A modacrylic copolymer of 35 to 85% by weight of acrylonitrile, 5 to 45% by weight of vinyl chloride, vinyl bromide, vinylidene chloride or a mixture thereof and 5 to 30% by weight of a carboxy phosphinic acid of the formula

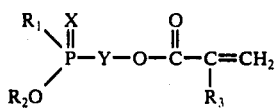

wherein R₁ and R₂ are alkyl or haloalkyl radicals having a total of up to 8 carbon atoms; R₃ is hydrogen or methyl; X is oxygen or sulfur; Y is linear or branched alkylene having up to 6 carbon atoms, and 0 to 15% by weight of other unsaturated compounds with activated double bond.

2. Flame-resistant filaments and fibers on the basis of modacrylic polymers wherein the fiber-forming substance comprises a copolymer of 35 to 85% by weight of acrylonitrile, 5 to 45% by weight of vinyl chloride, vinyl bromide, vinylidene chloride or a mixture thereof and 5 to 30% by weight of a carboxyphosphinic acid derivative of the formula

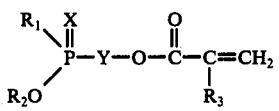

wherein R₁ and R₂ are alkyl or haloalkyl radicals having a total of up to 8 carbon atoms; R₃ is hydrogen or methyl; X is oxygen or sulfur; Y is linear or branched alkylene having up to 6 carbon atoms, and 0 to 15% by weight of other unsaturated compounds with activated double bond.

3. Flame-resistant filaments and fibers as defined in claim 2 and wherein the copolymer contains 8 to 20% by weight of the carboxyphosphinic acid derivative.

4. Flame-resistant filaments and fibers as defined in claim 2 and wherein R₁ and R₂ each have 1 to 4 carbon atoms.

5. Flame-resistant filaments and fibers as defined in claim 2 and wherein Y is alkylene of 1 to 3 carbon atoms.

* * * * *